United States Patent
Grumberg et al.

(12)
(10) Patent No.: US 6,398,705 B1
(45) Date of Patent: Jun. 4, 2002

(54) APPARATUS FOR SEPARATING PLASMA OR SERUM FROM THE RED CELLS WITH A BLOOD SAMPLE

(76) Inventors: Manfred Grumberg, 64 Dania Street, Haifa 34980; Oren Zinder, 3 Haim Hazzaz Street, Haifa 34996, both of (IL); James W. Winkelman, 62 Rangeley St., Brookline, MA (US) 02167; Jacob Schreibman, 45 Atzmon Street, Alfey-Menashe 44851 (IL)

( * ) Notice: Subject to any disclaimer, the term of this patent is extended or adjusted under 35 U.S.C. 154(b) by 0 days.

(21) Appl. No.: 09/661,131

(22) Filed: Sep. 13, 2000

Related U.S. Application Data

(63) Continuation-in-part of application No. 08/897,420, filed on Jul. 21, 1997, now Pat. No. 6,132,353, which is a continuation-in-part of application No. 08/734,235, filed on Oct. 21, 1996, now abandoned.

(51) Int. Cl.[7] .................................................. B04B 5/02
(52) U.S. Cl. .............................. 494/16; 494/47; 494/85
(58) Field of Search .............................. 494/16, 20, 31, 494/33, 34, 37, 38, 43, 47, 85; 210/416.1; 422/72

(56) References Cited

U.S. PATENT DOCUMENTS

| | | | | |
|---|---|---|---|---|
| 1,718,593 A | * | 6/1929 | Smith | |
| 1,928,998 A | * | 10/1933 | Kovacs | |
| 3,190,547 A | * | 6/1965 | Shanley et al. | |
| 3,494,508 A | * | 2/1970 | Hoefer | |
| 3,586,064 A | * | 6/1971 | Brown et al. | |
| 3,648,927 A | * | 3/1972 | Abbe et al. | |
| 3,654,925 A | * | 4/1972 | Holderith | |
| 3,771,965 A | * | 11/1973 | Grams | |
| 3,826,260 A | * | 7/1974 | Killinger | |
| 3,872,867 A | * | 3/1975 | Killinger | |
| 3,983,037 A | * | 9/1976 | Lee et al. | |
| 4,022,375 A | * | 5/1977 | Suovaniemi et al. | |
| 4,030,663 A | * | 6/1977 | Conn et al. | |
| 4,828,716 A | * | 5/1989 | McEwen et al. | |
| 4,853,137 A | * | 8/1989 | Ersson | |
| 5,037,549 A | * | 8/1991 | Ballies | |
| 5,096,573 A | * | 3/1992 | Bermudez | |
| 5,137,693 A | * | 8/1992 | Mawhirt | |
| 5,393,674 A | * | 2/1995 | Levine et al. | |
| 5,445,631 A | * | 8/1995 | Uchida | |
| 5,653,686 A | * | 8/1997 | Coulter et al. | |
| 6,234,948 B1 | * | 5/2001 | Yavilevich | |

* cited by examiner

*Primary Examiner*—Charles E. Cooley
(74) *Attorney, Agent, or Firm*—Mark M. Friedman

(57) ABSTRACT

The method of rapidly separating plasma or serum from red blood cells comprising the steps of mounting a pair of spaced apart tubes coaxially related to one another head-to-head with a sharp-ended hollow needle disposed generally along the tube axes and between them, arranging the tubes in a vertical position one above the other in a centrifuge with the tubes closed with self-sealing stoppers, providing a partial vacuum in the upper tube, rotating the tubes at high speed about an axis parallel to and spaced from the axis of the tubes and needle, after separation of the red blood cells from the plasma and serum causing the tubes while still being rotated to be moved relative to one another such as to cause the needle to enter both tubes through the stoppers, separating the tubes while still being rotated by the centrifuge whereby to remove the needle from both tubes.

21 Claims, 5 Drawing Sheets

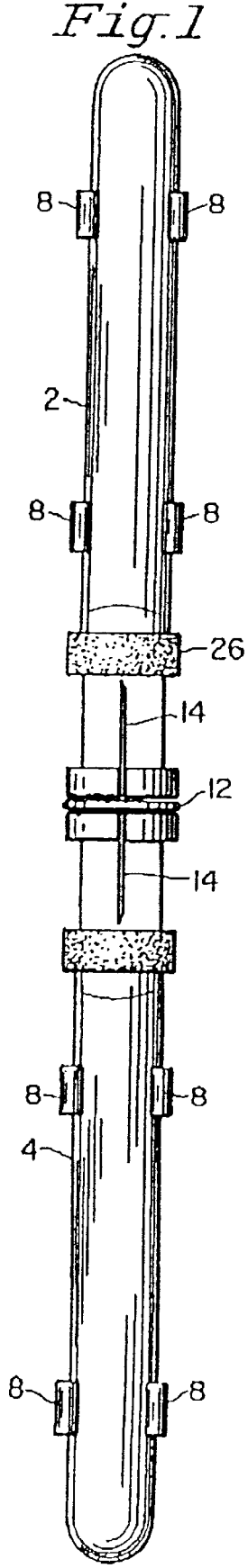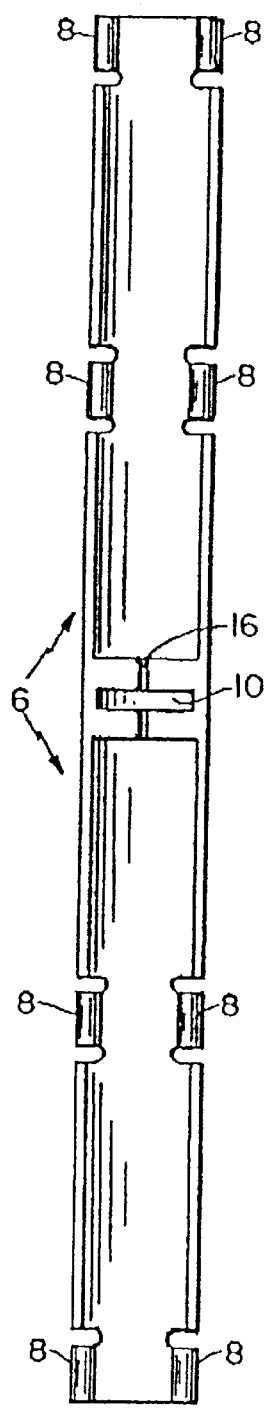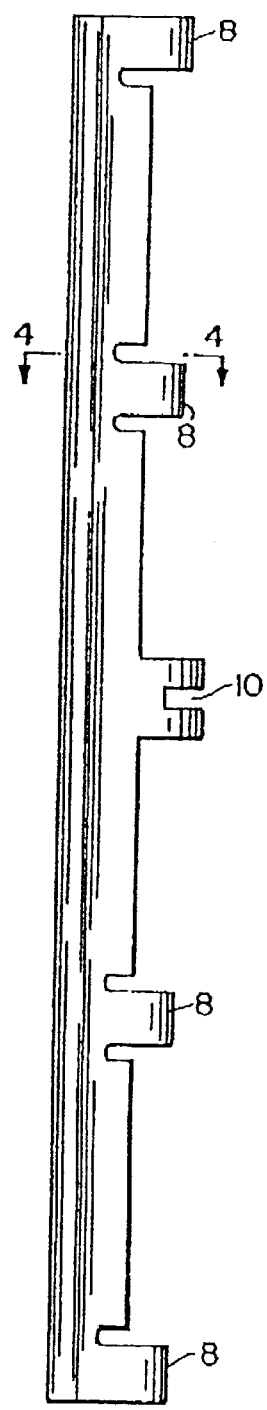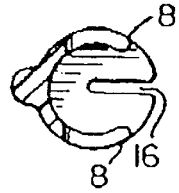

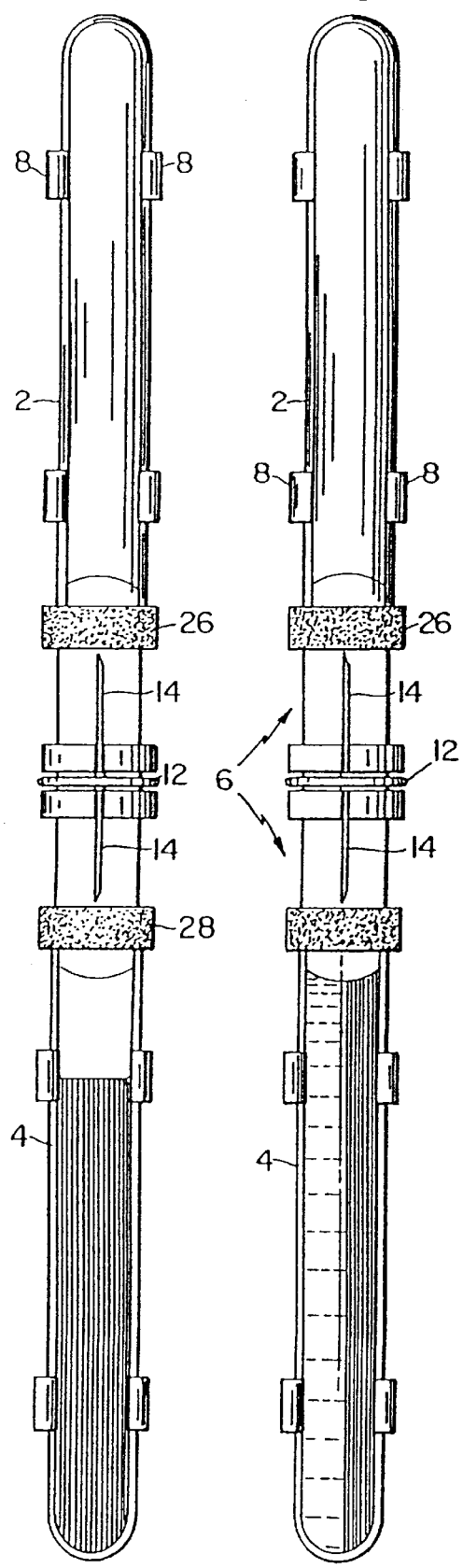
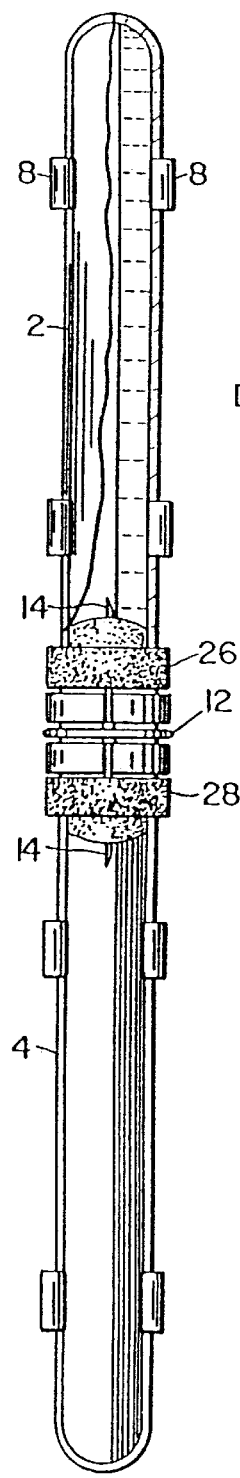
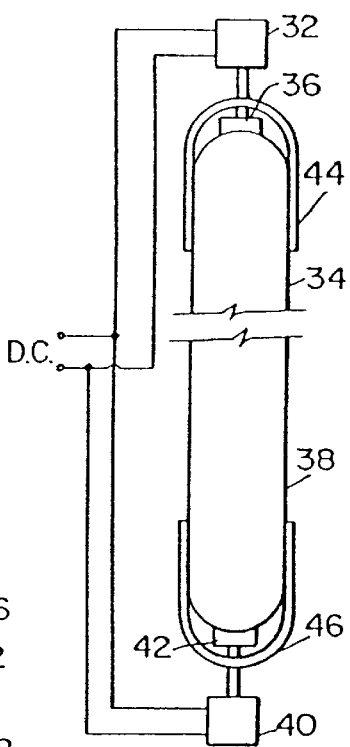

Fig.10
Fig.11
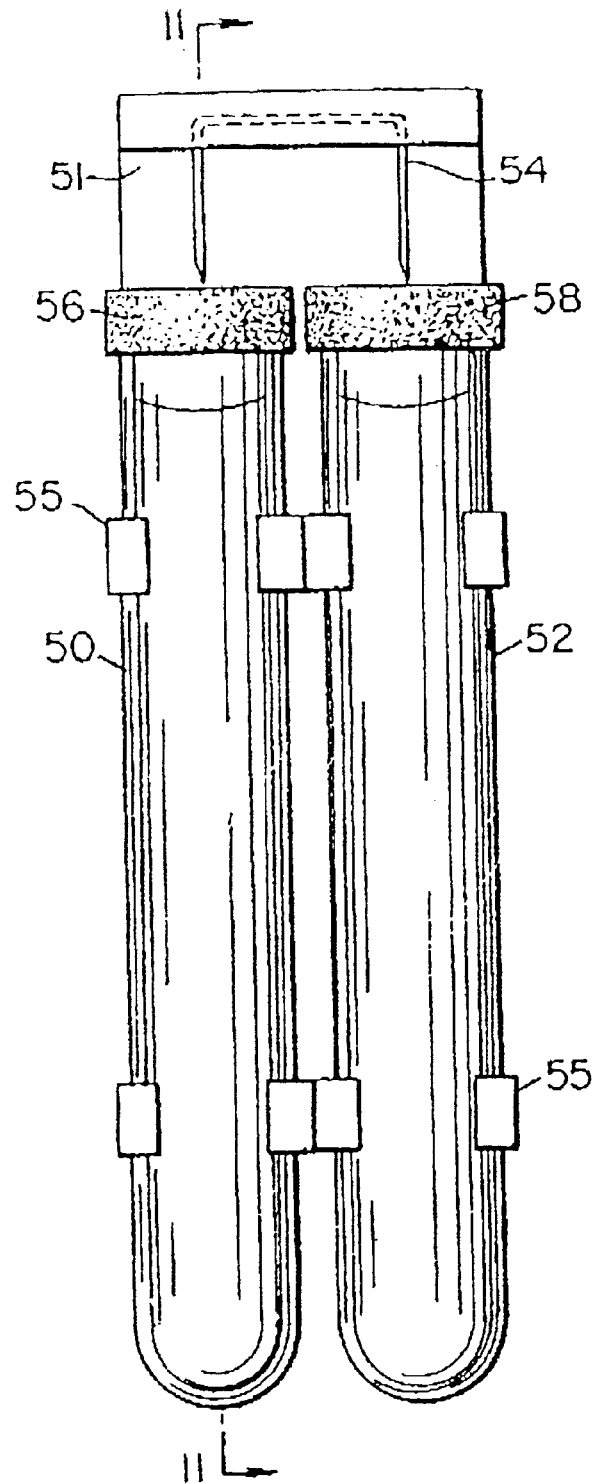
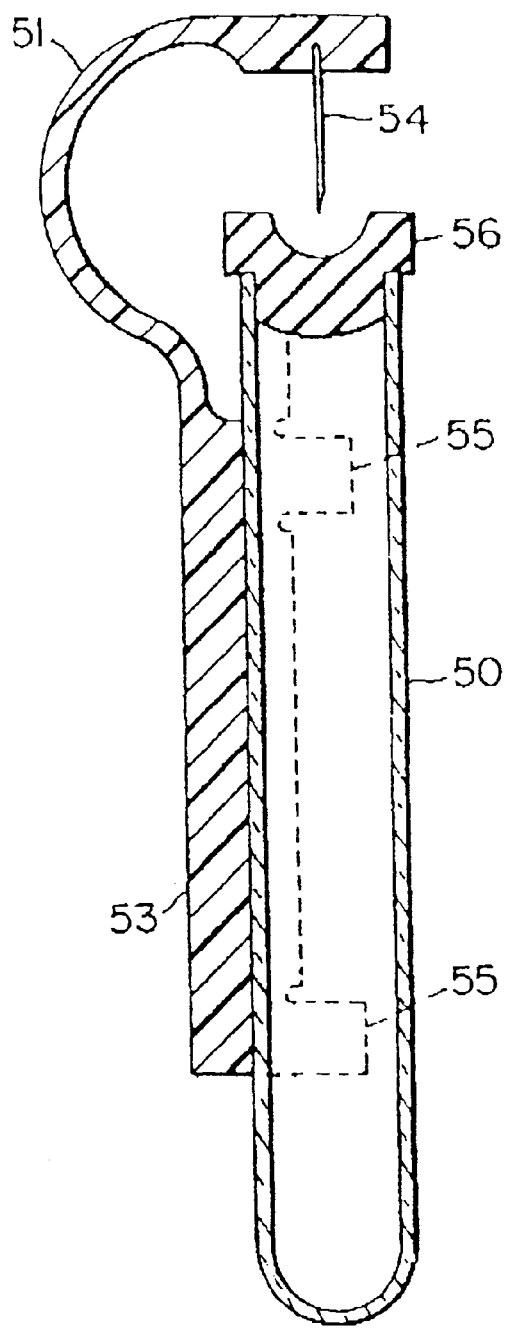

APPARATUS FOR SEPARATING PLASMA OR SERUM FROM THE RED CELLS WITH A BLOOD SAMPLE

This is a continuation-in-part of U.S. patent application Ser. No. 08/897,420 filed Jul. 21, 1997, now U.S. Pat. No. 6,132,353, which is a continuation-in-part of Ser. No. 08/734,235 filed Oct. 21, 1996, now abandoned.

FIELD OF THE INVENTION

The present invention relates to separation of plasma or serum from the red cells of a blood sample and more particularly to an apparatus and method for rapidly achieving such separation.

BACKGROUND OF THE INVENTION

In current practice plasma or serum is typically separated from the red blood cells of a blood sample by placing whole liquid or clotted blood respectively, in a tube, placing the tube in a swinging bucket type centrifuge which upon activation rotates rapidly and causes the tube to acquire a horizontal position. The red cells being heavier than the plasma or serum migrate to the end of the tube furthest from the center of rotation thus producing separation of the various components of the sample.

The above procedure is time consuming requiring extended periods of centrifuging to achieve the desired results because of the long migration path of the red cells.

U.S. Pat. No. 3,190,547 to J. J. Shanley discloses in FIGS. 10–13 a centrifuge wherein bottles are located below evacuated plasma receivers. The combination of each bottle and receiver is rotated together with other such combinations about an axis parallel to the axis of each combination, which axis passes through a bottle and receiver. In consequence red cells migrate upon rotation of the bottles about such axis toward the outer walls of the sample bottles. Upon completion of centrifuging the sample bottle and plasma receivers are connected through hollow needles situated in self-sealing stoppers in each member of the combination. The plasma is drawn into the plasma receivers which are then spun at a higher than previous rotational velocity separately from the now stationary specimen bottles to produce further separation of the materials drawn therein.

The mechanism is very complex requiring two separately driven rotating shafts, two different hollow needles to affect interconnection of the bottle and the receiver, rectangular shaped or other non-cylindrical specimen bottles to ensure that the bottles do not rotate about their own axes. This procedure further requires proper registration of the needle with the sample bottle. To provide proper alignment with the various strata in the specimen bottle, a readily movable self-sealing stopper in the specimen bottle is employed to assist in the search for the strata of the material desired. This procedure may require opening of the specimen bottle to locate the strata interface thus compromising the sterility of the specimen and possibly endangering the workers.

OBJECTS OF THE INVENTION

It is an object of the present invention to greatly shorten the time required to separate the components of either anticoagulated and/or clotted blood samples.

It is another object of the present invention to produce separation of the red blood cells from other components of whole blood in a system in which the plasma or serum at the end of the process is disposed in a separate container from the red cells.

Still another object of the present invention is to automatically separate serum or plasma into a different container from red blood cells from which the serum or plasma has been extracted.

Still another object of the present invention is to provide a quite simple assemblage for application to a centrifuge, the assemblage comprised of two test tubes, with self-sealing stoppers, a two ended hollow needle and a universal fixture to hold the tubes and needles in proper coaxial registration.

Yet another object of the present intention is to provide an apparatus for rapidly separating plasma or serum from blood samples by an assembly having a fixed structure of small size employing standard test tubes of the type employed by medical and paramedical personnel to withdraw blood from a patient.

It is another object of the invention to provide a fixture for holding the assemblage in registration, the fixtures all having a universal interface for registration with a centrifuge designed for such purpose and having a second interface that varies only with the dimensions of the test tubes. Thus loading and unloading of the centrifuge is simple and lends itself to automated input to and output from the machine. Also such arrangement increases safety by reducing the contact of laboratory personnel with the equipment and the danger of contact with potentially contaminated blood.

BRIEF SUMMARY OF THE PRESENT INVENTION

The preferred embodiment of the present invention is comprised of a spinning drum, which spins a plurality of pairs of head-to-head tubes held coaxially of one another and located around a vertical axis parallel to and spaced from the longitudinal center line of the tubes. Each pair of tubes is arranged head to head in which a primary tube contains blood while a collection tube is under vacuum and is empty. The primary or sample tube is located below the collection tube.

When the drum rotates, the red cells migrate a quite short distance to one side of the primary or sample tube. The separation time is quite short because of the shorter separating distance compared to the present method in which the cells are driven to the bottom of a tube, or in the Shanley patent to the walls of a 500 ml bottle. There is less chance of damage to the red cells due to the smaller radial pressure required. The use of small vessels such as test tubes has the advantage of more uniform pressure across the tube and thus a calculated maximum force may be employed without fear of damage to the specimens. Large vessels do not permit uniform pressures across the vessels so that lower average forces must be employed to insure that excessive pressure is not developed in the sample. Also in larger vessels separation may not be uniform as a result of non-uniform pressure.

The two tubes of each pair, in accordance with the present invention, the sample and collection tubes, are connected during the interval the drum is rotating by a single two sided hollow needle. The needle is introduced into the center of each of the tubes through self-sealing stoppers substantially simultaneously.

The plasma flows into the collection tube by reason of the partial vacuum in the collection tube and the pressure developed by the centrifuging action in the primary tube. It is to be noted that in humans the red cell and other non-plasma or serum volume of blood represents about 44% in males and 41% in females. The sample tube is usually not completely filled, 80% to 90% being the usual. At 90% with 44% red cells, only about 40% of the tube contains red cells thus providing a reasonable margin of safety. With a 41% red cell sample only 37% of the tube is filled with red cells. Thus the red cells and other non-serum or plasma materials are not near the center of the sample tube as a result of centrifuging and the two ended needle may be located along the center line of the tubes. Red cells are not available to the needle and therefore will not pass into the empty collecting tube. This feature provides a plasma or serum containing tube at the end of centrifuging suitable for use in the analytical determinations without any further serum or plasma transfer steps required. Further it is not necessary to perform any function that can compromise the sterility of the sample.

Further, in accordance with the preferred embodiment, there is a fixture which holds the two tubes facing each other and a hollow needle having two sharp ends in between. The tubes must have self-sealing stoppers or caps so that the blood flows only through the needle and does not spin out of the tubes. The tubes and needle can be snapped on or off the fixture manually or automatically. Further, the fixture with the tubes can be loaded or unloaded manually or automatically onto the drum. After the separation is completed and while the centrifuge is still spinning the two tubes are forced to slide towards each other so that the needle penetrates both stoppers allowing plasma to flow from the primary to the collection tube. The needle is preferably held by a disc that is snugly received by the fixture and may be made integral with the fixture. In all cases the needle should be a disposable item.

The collection tube can be labeled after it is placed in the fixture by any of several well known technologies such as laser printing directly onto the glass or plastic of the collection tube or on a sticky back label so that the collection tube label matches exactly a bar code or other code on a readable label previously applied to the sample tube. This approach assure positive specimen identification and replaces a step currently performed by other less dependable methods in which mislabeling of the collection tube can occur. Both tubes can be pre-labeled and the labeling verified upon insertion into the centrifuge by a computer or other suitable means.

Furthermore, the drum is provided with a plurality of bays, each of which can contain a fixture with tubes. The bay is directed inwardly opposite to the direction of rotation so that inertia forces the fixture into its designated position. The bays are designed, however, such that it is easy to replace the fixtures with the tubes by an external device that loads and unloads the centrifuge. The fixture can accommodate tubes of different sizes and different fixtures may be employed for different size tubes. The interface with the centrifuge remains the same.

Regardless of the nature of the sample, the above described assemblage is fully functional. If the sample has been drawn into a tube with an anticoagulant, it remains a liquid and the distribution is as stated above. If the sample is drawn into a tube without an anticoagulant the blood clotting proteins will polymerize about the blood platelets which had previously agglutinated, and after a predetermined time say, for instance, 10 minutes, will form a gelatinous mass or blood clot. This mass is usually formed directly in the sample tube and centrifuged. Since the distribution of red cells and related material in the clot and the serum is essentially the same as that of the red cells and plasma in a liquid sample, the assemblage remains the same. Thus regardless of the nature of the specimen or sample, the simple arrangement described above is completely suitable for the task.

As will become apparent subsequently the entire system is designed around the disposables; two test tubes, a needle and a couple of stoppers. The fixture may also be disposable. The geometry is slender, easily handled and provides short sample separation times. Further the system is designed for automation particularly since assembly of the tubes, fixture, etc. is quite simple.

The above and other features, objects and advantages of the present invention, together with the best means contemplated by the inventors for carrying out the invention will become more apparent from reading the following description of a preferred embodiment and perusing the associated drawings in which:

BRIEF DESCRIPTION OF THE DRAWINGS

FIG. 1 is a front view of the assembled containers, the needle and the fixture for holding the assembled containers;

FIG. 2 is a front view of the fixture;

FIG. 3 is a side view of the fixture;

FIG. 4 is a detail taken along section line 4—4 of FIG. 3;

FIG. 6 illustrates the tubes, fixture and needle with lower tube filled with whole blood;

FIG. 7 illustrates the separation of the blood components as a result of centrifuging;

FIG. 8 illustrates the position of the tubes upon transfer of materials;

FIG. 9 is a view of one of the chambers for holding a fixture, container and needle illustrating the location of the solenoids for bringing the containers together and for separating them;

FIG. 10 illustrates a different arrangement of the sample and collection tubes;

FIG. 11 is a side view of the apparatus of FIG. 10; and

DETAILED DESCRIPTION OF THE INVENTION

Figure 5:
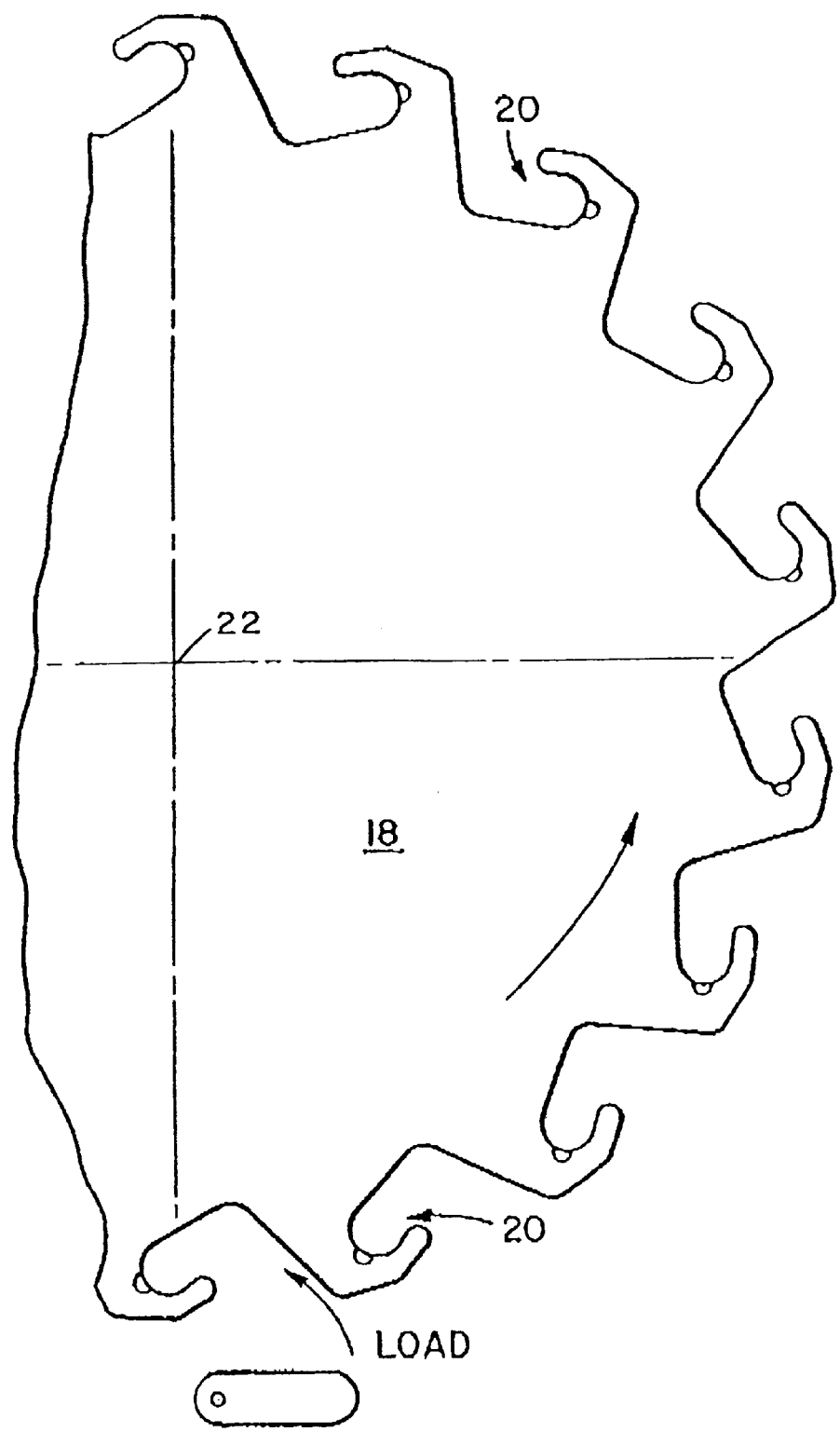
FIG. 5 is a top view of the part of the centrifuge for holding the fixtures, containers and needles.

Referring specifically to FIGS. 1–4 of the accompanying drawings, two tubes 2 and 4 are held head-to-head in a fixture 6. The fixture has several sets of opposed spring fingers 8 for grasping the tubes when inserted into the fixture 6. Two sets of spring fingers are illustrated for each tube. Located in the center of the fixture is a slot 10 for receiving a slotted needle holder 12. A needle 14 may be integral with fixture 6. The needle holder is insertable into horizontal slot 10 of FIGS. 1–3 with the needle seated in vertical channels 16, FIG. 2. Thus the needle is firmly held in place, FIG. 1. The position of the needle 14 and needle holder 12 is clearly illustrated in FIG. 1. FIG. 4 illustrates a slot 17 through which the needle passes as the needle holder 12 is inserted into slot 10. The needle, needle holder and fixture may be cast as a unit.

The assemblage is held together by the fixture 6 a slim simple device made of a spring type material so that all elements of the assemblage are firmly held in place. The stoppers and the test tubes are normally available in the industry and together with the needle and possibly the fixture are considered disposable. As previously indicated the structure is such that the needle may be and preferably is held along the center line of the tubes. The bevel of the needle is oriented away from the red cells. The fixture's spring fingers at one of its ends may be of a size to accommodate a tube of a different dimension from the fingers at its other end. Also the length of the needle may vary to accommodate tubes of different lengths and may fill the space between the stoppers.

Referring to FIG. 5, there is illustrated a region of the fixture holders 18 of a centrifuge. A fixture, such as fixture 6 of FIGS. 1–3, is insertable into each receiver 20 of a centrifuge having a plurality of receivers 20. The fixtures are situated with the center line of the tubes and needle parallel to spin center 22 of the centrifuge. The spin rate may be anywhere from 60 rps to 120 rps. The fixture 6 is of such structure as to interface with the centrifuge regardless of the sizes of the tubes. As can be seen in FIG. 5 the receivers 20 of the centrifuge may be or are identical and are provided with a notch 21 for receiving a projection 23 on the fixture 6, see FIG. 4, to stabilize the position of the structure in the receiver 20.

Both coagulated and uncoagulated blood may be processed at the same time so as to produce serum in the one instance and plasma in the other. The centrifuge as indicated above has numerous pockets and the sample in each pocket has no relationship to the samples in any of the other pockets so that both types of materials can be centrifuged concurrently. Thus plasma and/or serum can be the end product or products.

Reference is now made to FIGS. 6–8. In FIG. 6 tubes 2 and 4 are fully separated (extended) with liquid or coagulated whole blood in sample or lower tube 4. FIG. 7 illustrates the tubes after centrifuging with the red cells compacted against the region of the tube wall remote from the center of rotation of the centrifuge. The red cells constitute only about 37% to a maximum of about 44% in the latter case if the tube is fully filled. Thus the center 25 of the lower tube 4 rarely if ever contains red cells as a result of centrifuging for a time necessary to effect complete separation, one minute or less in a standard size tube.

Referring now to FIG. 8 of the accompanying drawings, the tubes 2 and 4 have been pushed together causing needle 14 to penetrate self-sealing stoppers 26 and 28 and establish communication between tubes 2 and 4. The vacuum in tube 2 and the pressure created by centrifuging in the sample tube causes the plasma or serum, to be transferred to the upper tube 2. Thereafter the tubes may be separated while the centrifuge is still rotating, the stoppers 26 and 28 sealing their respective tubes. The centrifuge may now be stopped, the fixture(s) with tubes may be removed and the tubes processed separately thereafter. If the material remaining in the sample tube is not to be used the sample tube may also be discarded.

Referring to FIG. 9, a solenoid 32 is connected to a cap 44 that is disposed about the top of upper tube 34 of an array employed in the present invention. A plate 36 presses on the top of the tube 34 to force it down to cause the upper tube 34 to move toward lower tube 38. Concurrently solenoid 40 is energized to move lower tube 38 upward whereby the tubes 34 and 38 assume the position of FIG. 6 hereof.

On the end of each solenoid shaft is an elastic sleeve with the plate 36 of solenoid 32 at the upper end of the structure as viewed in FIG. 9. There is a corresponding plate 42 of solenoid 40 disposed inside of sleeve 46. Upon reversal of polarity to the solenoids, the needle is withdrawn from the tubes.

It is not necessary that the needle be coaxial with the tubes. The needle may be off center away from the side of the tubes in which the red cells are collected to further insure in those rare instances that red cells may be near the center so that none of the red cells are drawn into the upper tube. Such an occurrence is quite uncommon if not essentially impossible. Note the level of the needle away from the red cells. Further, location of the collection tube above the sample tube permits gravity to assist in the separation of the heavier red cells from the plasma and serum. It is not necessary that the two tubes be of the same length or diameter. A fixture may be provided that can accommodate different size tubes or different fixtures may be provided for each different combination of test tubes or a test tube and plastic tubing. It is not necessary that the upper tube be a test tube. It can be a hose (plastic tubing) connected, for instance, to a vacuum pump that is energized at approximately the same time as the solenoid to produce puncture of the self-sealing stopper by the needle. The hose discharges into a suitable container.

Figure 12:
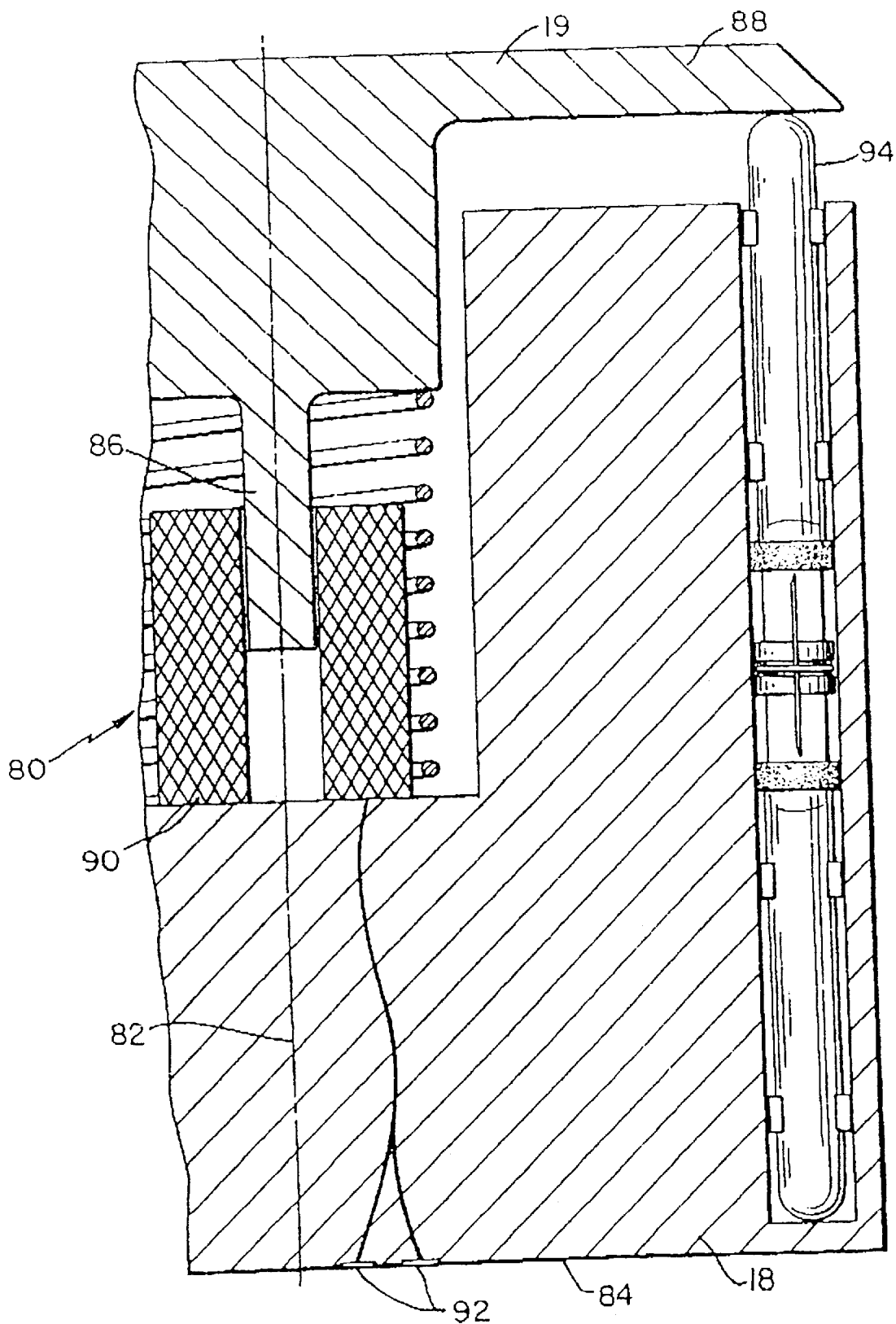
FIG. 12 illustrates a structure for causing all of the needles of various structures in the pockets of a centrifuge to pierce their associated tube structures concurrently.

Referring now to FIG. 10 of the accompanying drawings, there is illustrated an arrangement of standard sample and receiver tubes 50 and 52, respectively, arranged side by side. The tubes 50 and 52 are held by spring fingers 55 of a fixture 53 that is insertable into pockets of a centrifuge. A U-shaped needle 54 is positioned above stoppers 56 and 58 of both tubes and is attached to a leaf spring 51 so as to be poised above the stoppers. Depression of the springs, as by the apparatus of FIG. 12, connects the tubes 50 and 52.

It is apparent that at no time in the procedure is the sample, the serum or the plasma exposed to the air and thus its contents cannot reach the external environment. The risk is eliminated to blood workers of exposure to disease causing microorganisms in blood in this step that otherwise could occur upon removal of the stopper from either tube. Removal of a stopper is accompanied by formation of droplets or aerosol from liquid blood or clots during manual transfer of plasma or serum to a secondary collection tube.

The arrangement of FIG. 9 is acceptable for a single pocket arrangement but would be awkward for a multiple pocket arrangement. The structure of FIG. 12, however, is suitable for multiple pockets. In this structure a solenoid 80 is symmetrical with respect to axis 82 of the centrifuge 84. Armature 86 of the solenoid 80 provides across its top a plate 88 that lies about all of the pockets of the centrifuge. Coil 90 of the solenoid 80 is connected through slip rings 92 located on a surface of the centrifuge.

The armature 86 and its plate 88 are biased upwardly as viewed in FIG. 11 but upon energization of the solenoid the armature is retracted into the coil 90 and the plate presses down on receiver tubes 94 of tube and fixture structures located in the pockets of the centrifuge. The sleeve arrangement of FIG. 9 may be employed to extract the needle from the tubes.

The geometry of this system or assemblage is remarkably simple, the fixture 6 is responsible for and does at all times maintain the assemblage. The assemblage can handle both coagulated and uncoagulated blood in the centrifuge at the same time. The structure is designed around inexpensive disposables. Further because of its slim design it can produce separation of red cells, etc. from serum or plasma in a matter of approximately one minute or less at speeds of 60 to 120 rps. In still another arrangement the collection tube may be integral with the fixture.

Once given the above disclosure, many other features, modifications and improvements will become apparent to the skilled artisan. Such features, modifications and improvements are, therefore, considered to be a part of this invention, the scope of which is to be determined by the following claims.

What is claimed is:

1. A structure comprising:
   at least one pair of first and second hollow cylindrical members, each of said cylindrical members having one end closed and a stopper closing another end,
   first means, including a fixture for holding said cylindrical members side by side,
   at least one hollow needle sharp at both ends, said sharp ends of said at least one needle disposed adjacent said stoppers of said cylindrical members and disposed approximately along an axis of each of said cylindrical members, each of said sharp ends for piercing one said stoppers,
   a centrifuge having a spin axis parallel to said axis of said cylindrical members,
   said centrifuge having a plurality of pockets along an outer circumference thereof,
   each of said pockets operative for receiving a pair of said cylindrical members and said at least one needle, and
   second means on said centrifuge for concurrently causing said at least one needle of said at least one pair to pierce both of said stoppers.

2. A centrifuge and plasma or serum separation arrangement comprising:
   a tube and holder structure, and
   means for rotating the tube and holder structure at high speed; said tube and holder structure including:
      (a) a first tube having a longitudinal axis, said first tube for receiving a fluid to be separated into its various components,
      (b) a stopper closing a first end of said first tube,
      (c) a second tube having a longitudinal axis,
      (d) a hollow needle for piercing said stopper, and
      (e) an integral holder for holding said tubes and said needle in one of an opposed or side by side relation with respect to one another,
   wherein said means for rotating rotates the tube and holder structure about an axis substantially parallel to said longitudinal axes, and wherein said tube and holder structure is selectively placed into and removed from said means for rotating the tube and holder structure.

3. The separation arrangement according to claim 2, wherein said tube and holder structure is designed and configured for automatic loading and unloading of said tubes.

4. The separation arrangement according to claim 2, wherein said needle is sharp at both ends.

5. The separation arrangement according to claim 2, wherein said stopper is a self-sealing stopper.

6. The separation arrangement according to claim 2, the arrangement further comprising:
   a second stopper closing a first end of said second tube.

7. The separation arrangement according to claim 2, wherein said needle is a single-use, disposable needle.

8. The separation arrangement according to claim 2, wherein said tubes are single-use, disposable tubes.

9. The separation arrangement according to claim 2, the arrangement further comprising
   means for bringing said tubes toward one another sufficiently to cause said needle to penetrate said stopper and operatively connect said tubes.

10. The separation arrangement according to claim 9, said means for bringing said tubes including means for subsequently separating said tubes.

11. The separation arrangement according to claim 2, the arrangement further comprising
    means for separating said tubes while said means for rotating continues to operate at high speed.

12. The separation arrangement according to claim 2, further comprising
    a generally round member having an axis of rotation and a circumference providing a plurality of pockets, said round member being operatively connected to said means for rotating the tube and holder structure,
    each of said pockets adapted to receive said tube and holder structure,
    wherein each said tube and holder structure is situated such that said longitudinal axes of said tubes are parallel to and offset from said axis of rotation of said round member.

13. The separation arrangement according to claim 2, wherein said tube and holder structure has spring fingers for holding said tubes.

14. The separation arrangement according to claim 13, wherein said spring fingers adapt said tube holder structure to tubes of different sizes.

15. The separation arrangement according to claim 2, wherein said tube and holder structure holds said tubes in opposed relation.

16. The separation arrangement according to claim 2, wherein said tube and holder structure holds said tubes in side by side relation.

17. A centrifuge and plasma or serum separation arrangement comprising:
    a tube structure including:
       a first tube having a longitudinal axis,
       said first tube for receiving a fluid to be separated into its various components,
       a stopper closing a first end of said first tube,
       a second tube having a longitudinal axis and having a first end,
       a hollow needle for piercing said stopper;
       a holder for holding said tubes and said needle in a collinear fashion with respect to one another, and
       means for rotating the tube structure at high speed about an axis substantially parallel to said longitudinal axes,
    wherein said holder includes:
       a long narrow spine,
       a plurality of spring fingers spaced along a length of said spine and extending from said spine,
       said fingers having a shape to engage and hold said tubes,
       outwardly extending rigid fingers located between at least two of said fingers, and defining a slot perpendicular to said length of said spine,
       a disc,
       said slot dimensioned to snugly receive said disc,
       said slot defined by top and bottom members having aligned narrow recesses located along an axis parallel to said tubes to be held by said spring fingers.

18. The separation arrangement according to claim 17, wherein said needle passes through a hole in said disc and being aligned with said axis of said tubes and with said aligned narrow recesses.

19. A structure comprising:
    a plurality of sample holders each having a first axis,
    a centrifuge having a member rotatable at high speed about a second axis,
    said member having a plurality of pockets displaced from said second axis, each of said pockets disposed to receive one of said sample holders, a plurality of specimen receivers, each of said specimen receivers forming a pair with one of said sample holders, self-sealing stoppers in each of said sample holders and said specimen receivers, each of said plurality of specimen receivers having a hollow needle having two sharp ends, each of said sharp ends for piercing both said self-sealing stoppers, means for holding each said hollow needle in one of an opposed or side by side relation with said first axis of each of said holders and said specimen receivers, means holding each said pair of said sample holders and said specimen receivers in a different one of said pockets, with said axis of said sample holders situated in parallel to said second axis, wherein said pockets are directed inwardly, such that each of said sample holders is secured into a designated position within each of said pockets.

20. A structure comprising:

a plurality of sample holders each having a first axis, a centrifuge having a member rotatable at high speed about a second axis, said member having a plurality of pockets displaced from said second axis, each of said pockets disposed to receive one of said sample holders, a plurality of specimen receivers, each of said specimen receivers forming a pair with one of said sample holders, self-sealing stoppers in each of said sample holders and said specimen receivers, each of said plurality of specimen receivers having a hollow needle having two sharp ends, each of said sharp ends for piercing both said self-sealing stoppers, means for holding each said hollow needle in one of an opposed or side by side relation with said first axis of each of said holders and said specimen receivers, means holding each said pair of said sample holders and said specimen receivers in a different one of said pockets, with said axis of said sample holders situated in parallel to said second axis, and an outwardly extending projection from each of said sample holders, each of said pockets having means to engage said projection to maintain an orientation of said sample holders in said pockets.

21. A structure comprising:

a plurality of sample holders each having a first axis, a centrifuge having a member rotatable at high speed about a second axis, said member having a plurality of pockets displaced from said second axis, each of said pockets disposed to receive one of said sample holders, a plurality of specimen receivers, each of said specimen receivers forming a pair with one of said sample holders, self-sealing stoppers in each of said sample holders and said specimen receivers, each of said plurality of specimen receivers having a hollow needle having two sharp ends, each of said sharp ends for piercing both said self-sealing stoppers, means for holding each said hollow needle in one of an opposed or side by side relation with said first axis of each of said holders and said specimen receivers, means holding each said pair of said sample holders and said specimen receivers in a different one of said pockets, with said axis of said sample holders situated in parallel to said second axis, and means including said means holding each said pair amid said pockets for maintaining an orientation of said sample holders as initially placed in said pockets.

* * * * *